(12) United States Patent
Laskin et al.

(10) Patent No.: US 7,150,967 B2
(45) Date of Patent: Dec. 19, 2006

(54) FLUORESCENT TAGS FOR AMINO ACID AND NUCLEIC ACID ANALYSIS

(75) Inventors: Jeffrey D. Laskin, Piscataway, NJ (US); Christine Martey, Harrisburg, PA (US); Ned Heindel, Easton, PA (US); Marilyn Whittemore, Germantown, TN (US); Diane Heck, Rumson, NJ (US)

(73) Assignees: University of Medicine & Dentistry of New Jersey, New Brunswick, NJ (US); Rutgers, the State University, New Brunswick, NJ (US); Lehigh University, Bethlehem, PA (US); Buckman Laboratories International, Inc., Memphis, TN (US)

( * ) Notice: Subject to any disclaimer, the term of this patent is extended or adjusted under 35 U.S.C. 154(b) by 396 days.

(21) Appl. No.: 10/408,170

(22) Filed: Apr. 4, 2003

(65) Prior Publication Data
US 2004/0018517 A1    Jan. 29, 2004

Related U.S. Application Data

(60) Provisional application No. 60/370,951, filed on Apr. 8, 2002.

(51) Int. Cl.
C12Q 1/68     (2006.01)
G01N 33/53    (2006.01)
C07H 21/00    (2006.01)
C07K 17/00    (2006.01)

(52) U.S. Cl. .............. 435/6; 435/7.1; 435/7.2; 536/23.1; 536/24.3; 536/26.6; 530/300; 530/350

(58) Field of Classification Search .......... 435/6, 435/7.1, 7.2; 536/23.1, 24.3, 26.6; 530/300, 530/350
See application file for complete search history.

(56) References Cited

U.S. PATENT DOCUMENTS

| 4,279,992 | A | 7/1981 | Boguslaski et al. .......... 435/7 |
| 4,956,480 | A | 9/1990 | Robinson .................. 549/288 |
| 5,188,934 | A | 2/1993 | Menchen et al. ............. 435/6 |
| 5,248,782 | A | 9/1993 | Haugland et al. .......... 548/110 |
| 5,268,486 | A | 12/1993 | Waggoner et al. ......... 548/427 |
| 5,274,113 | A | 12/1993 | Kang et al. ............... 548/405 |
| 5,371,241 | A | 12/1994 | Brush ....................... 549/220 |
| 5,433,896 | A | 7/1995 | Kang et al. ............... 252/700 |
| 5,437,980 | A | 8/1995 | Haugland .................... 435/6 |
| 5,442,045 | A | 8/1995 | Haugland et al. ....... 530/391.3 |
| 5,451,663 | A | 9/1995 | Kang et al. ............... 530/367 |
| 5,583,236 | A | 12/1996 | Brush ....................... 549/220 |
| 5,627,027 | A * | 5/1997 | Waggoner .................... 435/6 |
| 5,654,442 | A | 8/1997 | Menchen et al. .......... 549/223 |
| 5,658,735 | A | 8/1997 | Lee .......................... 435/6 |
| 5,696,157 | A | 12/1997 | Wang et al. ............... 514/457 |
| 5,700,921 | A * | 12/1997 | Westling et al. .......... 536/22.1 |
| 6,255,324 | B1 | 7/2001 | Heindel et al. ............ 514/314 |
| 6,291,203 | B1 | 9/2001 | Poot et al. ................ 435/40.5 |
| 6,299,055 | B1 | 10/2001 | Pitel ......................... 228/175 |
| 6,335,446 | B1 | 1/2002 | Pennington et al. ....... 544/359 |

OTHER PUBLICATIONS

Saffran et al. "Site-directed psoralen crosslinking of DNA" Proc. Natl. Acad. Sci. USA, vol. 79, pp. 4594-4598, 1982.*
Naveenan et al. "Reactive Thiol Grooups in Rat Liver Acid Phosphatase" Enzyme 33, pp. 197-204 1985.*
Song et al., "Labeling of Nucleic Acids with Psoralens", Annals New York Acad. Sci. 1980 346:355-367.
Chapter 2 of the commerical catalog for Molecular Probes, Inc. Richard Haugland, Handbook of Fluorescent Probes and Research Chemicals, 6th Edition 1996.

* cited by examiner

*Primary Examiner*—Jezia Riley
(74) *Attorney, Agent, or Firm*—Licata & Tyrrell P.C.

(57) ABSTRACT

Methods and kits for labeling and detecting thiol containing species and nucleic acids using mercurimethyl-dihydropsoralen compounds and derivatives thereof which intercalate nucleic acids and are highly reactive with thiol containing species are provided. Fluorescent reactions products of the mercurimethyl-dihydropsoralen compounds or derivatives thereof attached to a thiol containing species and nucleic acids fluorescently labeled with these reaction products are also provided.

9 Claims, No Drawings

FLUORESCENT TAGS FOR AMINO ACID AND NUCLEIC ACID ANALYSIS

This application claims the benefit of provisional U.S. application Ser. No. 60/370,951, filed Apr. 8, 2002, which is herein incorporated by reference in its entirety.

INTRODUCTION

This invention was supported in part by funds from the U.S. government (NIH Grant Nos. ES03647, ES06897 and ES05022) and the U.S. government may therefore have certain rights in the invention.

FIELD OF THE INVENTION

The present invention relates to compounds useful for fluorescent labeling and detection. In particular, nucleic acid intercalating mercurimethyl-dihydropsoralen compounds and derivatives thereof such as mercurimethyl-angelicin compounds are provided which are highly reactive with thiol containing species. The product of the reaction of the mercurimethyl-dihydropsoralen compounds or derivatives thereof with a thiol containing species is highly fluorescent.

BACKGROUND OF THE INVENTION

Fluorescent dyes or tags are used in various applications as highly sensitive detection reagents. Fluorescent dyes or tags that preferentially label a selected component of a sample can be used to determine the presence, quantity or location of that selected component. For example, thiol reactive probes such as BODIPY, fluorescein, Oregon Green, tetramethylrhodamine and Texas Red are use routinely to fluorescently label proteins and polypeptides as these probes react readily with the thiol groups, also called mercaptans or sulfhydryls, present in cysteine residues. Additional examples of thiol reactive probes are set forth in Chapter 2 of the commercial catalog for Molecular Probes, Inc. (Richard Haugland, Handbook of Fluorescent Probes and Research Chemicals, 6th Edition 1996 Molecular Probes, Eugene, Oreg., pp. 47–62).

Various other compounds for use as fluorescent tags have also been described. See, for example, U.S. Pat. No. 6,335,446 describing quinolinium- and pyridinium-based fluorescent dyes; U.S. Pat. No. 6,299,055 describing fluorinated xanthine derivatives; U.S. Pat. No. 6,291,203, U.S. Pat. No. 5,658,735 and U.S. Pat. No. 5,268,486 describing cyanine dyes; U.S. Pat. No. 5,654,442 and U.S. Pat. No. 5,188,934 describing 4,7-dichlorofluorescein dyes; U.S. Pat. No. 5,451,663, U.S. Pat. No. 5,248,782 and U.S. Pat. No. 5,274,113 describing heteroaryl-substituted dipyrrometheneboron difluoride dyes and U.S. Pat. No. 5,433,896 describing dibenzopyrromethenboron difluoride dyes; U.S. Pat. No. 5,583,236 and U.S. Pat. No. 5,371,241 describing fluorescein labeled phosphoramidites; U.S. Pat. No. 5,437,980 describing phenanthridium dyes; and U.S. Pat. No. 5,442,045 describing biological conjugates of fluorescent rhodol dyes.

Coumarin derivatives are used widely as fluorescent labels or tracers and in the preparation of fluorogenic substrates for enzymes, particularly when a fluorophore having excitation in the ultraviolet and generally blue to blue-green fluorescent emission range is desired. U.S. Pat. No. 4,956,480 discloses 3-carboxyalkyl derivatives of 7-amino-4-methylcoumarin and U.S. Pat. No. 4,279,992 discloses 7-hydroxycoumarin or umbelliferone for use as fluorescent labels or tags. However coumarin dyes are not particularly soluble in the aqueous environment of most biological systems. Further, their fluorescence is often unstable over periods of extended use and is quenched upon conjugation, particularly to proteins.

U.S. Pat. No. 5,696,157 discloses fluorescent sulfonated derivatives of 7-aminocoumarin that remain bright upon conjugation and exhibit photostability and enhanced aqueous solubility.

Furocoumarin compounds, more commonly known as psoralens, have been used for centuries in combination with ultraviolet light in cosmetics and for the treatment of proliferative skin disorders such as eczema, vitiligo, psoriasis, and mycosis fungoides. More recently, this photosensitive therapy has been used to treat cancer, in particular T cell lymphoma, autoimmune diseases, and microbial infection.

Psoralens intercalate into DNA in the cell nucleus and subsequently enter into photo-induced crosslinking with the DNA by forming 2+2, cyclobutane fusions from double-bonds in the psoralen to double bonds in the pyrimidine bases.

Psoralens (furocoumarins) can also be used as photo reactive nucleic acid stains for probing DNA and RNA structures. 4,5',8-Trimethylpsoralen, psoralen, 5-methoxypsoralen and 8-methoxypsoralen intercalate into double-stranded DNA where, upon illumination with ultraviolet light of wavelengths from 320 to 400 nm (ultraviolet light A or UVA), they covalently bind to pyrimidines (Annals NY Acad. Sci. 1980 346:355). However, like other coumarins, the intrinsic blue fluorescence of these compounds is usually quenched upon binding to the target.

5'-substituted, 4',5'-dihydropsoralen compounds bearing organomercurial moieties and methods for their production are described in U.S. Pat. No. 6,255,324, the teachings of which are herein incorporated by reference in its entirety. These compounds are taught to be useful in the treatment of proliferative skin disorders and diseases of the blood and bone marrow, as well as antimicrobial agents.

It has now been found that these mercurimethyl-dihydropsoralen compounds and derivatives thereof are highly reactive with thiol containing species. Further, the reaction product is highly fluorescent. Accordingly, these compounds are useful as fluorescent tags for labeling and detection of thiol containing species, in particular amino acids, proteins and peptides. In addition, the fluorescent thiol containing reaction products maintain their ability to intercalate into nucleic acid sequences, thus also providing a fluorescent tag for labeling and detection of nucleic acids.

SUMMARY OF THE INVENTION

An object of the present invention is to provide mercurimethyl-dihydropsoralen compounds and derivatives thereof which are highly reactive with thiol containing species and produce an intensely fluorescent product upon reaction.

Another object of the present invention is to provide a method for fluorescently labeling a thiol containing species which comprises reacting the thiol containing species with a mercurimethyl-dihydropsoralen compound or a derivative thereof.

Accordingly, another object of the present invention is to provide a fluorescently labeled reaction product comprising a thiol containing species covalently bound to a mercurimethyl-dihydropsoralen compound or a derivative thereof.

Another object of the present invention is to provide a method for detecting thiol containing species in a sample which comprises contacting a sample suspected of containing a thiol containing species with a mercurimethyl-dihydropsoralen compound or a derivative thereof so that the mercurimethyl-dihydropsoralen compound or the derivative thereof reacts with any thiol containing species in the sample; and detecting fluorescence, wherein fluorescence is indicative of a thiol containing species in the sample.

Another object of the present invention is to provide a method for detecting nucleic acids which comprises contacting a sample suspected of containing nucleic acid sequences with a fluorescently labeled reaction product comprising a thiol containing species and a mercurimethyl-dihydropsoralen compound or a derivative thereof so that the fluorescently labeled reaction product intercalates into any nucleic acids in the sample, and detecting fluorescence, wherein fluorescence is indicative of a nucleic acid in the sample.

Another object of the present invention is to provide a fluorescently labeled nucleic acid sequence comprising a nucleic acid sequence and a fluorescently labeled reaction product of a thiol containing species attached to a mercurimethyl-dihydropsoralen compound or a derivative thereof which intercalates into the nucleic acid sequence.

Yet another object of the present invention is to provide kits comprising a mercurimethyl-dihydropsoralen compound or a derivative thereof or a reaction product comprising a mercurimethyl-dihydropsoralen compound or a derivative thereof and a thiol containing species for fluorescently labeling thiol containing species or nucleic acids and/or detecting thiol containing species or nucleic acids.

DETAILED DESCRIPTION OF THE INVENTION

Fluorescent compounds are used widely to detect a variety of proteins and nucleic acids. For example, fluorescent compounds are used routinely in diagnostic assays, DNA sequencing and profiling technologies, genomic analysis, protein identification, antibody binding and metabolite analysis.

The present invention provides mercurimethyl-dihydropsoralen compounds and derivatives thereof such as mercurimethyl-angelicin compounds which are highly reactive with thiol containing species and produce an intensely fluorescent product upon reaction with a thiol containing species. Accordingly, the mercurimethyl-dihydropsoralen compounds and derivatives thereof can be used to label and/or detect minute quantities of thiol containing species such as amino acids, proteins and polypeptides. In addition, it has been found that mercurimethyl-dihydropsoralen compounds and derivatives thereof, when reacted with a thiol containing species such as cysteine or glutathione (GSH), maintain their ability to act as nucleic acid intercalating agents. Accordingly, fluorescent reaction products comprising a mercurimethyl-dihydropsoralen compound or derivative thereof and a thiol containing species can also be used to fluorescently label and/or detect nucleic acids in biological samples. Thus, mercurimethyl-dihydropsoralen compounds and derivatives thereof are useful in various methods including, but not limited to, clinical diagnostic assays, detection of nucleic acids in sequence analysis and gene profiling, detection of selected proteins by fluorescent microscopy, and detection of free thiols.

For purposes of the present invention, by "thiol containing species" it is meant any molecule with a thiol, mercaptan or sulfhydryl group which reacts with a mercurimethyl-dihydropsoralen compound or a derivative thereof to form a fluorescent reaction product. Examples include, but are not limited to, amino acids, peptides and proteins. By amino acid it is meant to include natural amino acids, preferably sulfhydryl containing amino acids including, but not limited to cysteine, cystine and methionine, and their optical isomers, as well as synthetic variations well known in the art. Examples of such synthetic variations include, but are not limited to, amino acids that are protected on their amino, carboxylic acid, hydroxy, thiol, imidazole, or other functional group, modified amino acids which are substituted by phosphate or through glycosylation or acylation with a carboxylic acid. By peptide it is generally meant an amino acid sequence of preferably about 5 to about 35 amino acids and having a molecular weight of about 10,000 daltons or less. Examples of peptides that can be fluorescently labeled and/or detected using the present invention include, but are in no way limited to, neuropeptides, chemotactic peptides, cytokines, lymphokines, gastrointestinal peptides, toxins, protease substrates, synthetic peptides, experimental peptides, endothelin, and protein kinase substrates. By protein it is generally meant an amino acid sequence greater than 35 amino acids and having a molecular weight of 5,000 daltons or greater. Typically proteins will also have secondary, tertiary and/or quaternary structure. Examples or proteins which can be fluorescently labeled and/or detected using the present invention include, but are in no way limited to, enzymes, antibodies and antibody fragments, kinases, lectins, glycoproteins, albumins, lipoproteins, avidin, streptavidin, phycobiliproteins, hormones, toxins, and growth factors.

By "nucleic acid sequence" as used herein, it is meant a double-stranded nucleic acid sequence of sufficient length, preferably at least 5 nucleotides, such that the mercurimethyl-dihydropsoralen or derivative thereof can intercalate into the nucleic acid sequence. The nucleic acid sequence may comprise DNA, RNA or a mixture thereof. The DNA or RNA may comprises natural nucleotides as well as nucleotides which have been modified.

Mercurimethyl-dihydropsoralen compounds for use in the present invention and methods for their production are described in detail in U.S. Pat. No. 6,255,324, the teachings of which are herein incorporated by reference in their entirety. Derivatives of mercurimethyl-dihydropsoralen such as mercurimethyl-angelicins are described by M. Whittemore, in the Ph.D. thesis entitled "Synthesis, structure-activity relationships and photochemical studies of novel coumarins, hydropsoralens and dihydroangelicins as photoactivated agonists of the psoralen receptor (Lehigh University, 1998). Exemplary mercurimethyl-dihydropsoralen compounds and mercurimethyl-angelicin compounds useful in the present invention are also depicted in Table 1.

TABLE 1

Mercurimethyl-dihydropsoralen and mercurimethyl angelicin compounds

| Compound | Structure |
| --- | --- |
| P1 iodomercurio-$H_2$DMP | (structure) |
| P2 chloromercurio-$H_2$DMP | (structure) |
| P3 trifluoro-acetylmercurio-$H_2$DMP | (structure) |
| P4 acetylmercurio-$H_2$DMP | (structure) |
| P5 3-fluoro-acetylmercurio-$H_2$DMP | (structure) |
| P6 3-cyano-acetylmercurio-$H_2$DMP | (structure) |
| P7 iodomercurio angelicin | (structure) |

TABLE 1-continued

Mercurimethyl-dihydropsoralen and mercurimethyl angelicin compounds

| Compound | Structure |
| --- | --- |
| P8 acetylmercurio angelicin | (structure of acetylmercurio angelicin with CH₃, fused pyranone-furan ring system, and -CH₂-Hg-O-C(=O)-OMe side chain) |

The ability of mercurimethyl-dihydropsoralen compounds to react with a thiol containing species and produce a new reaction product was demonstrated with the thiol containing species bovine serum albumin (BSA). BSA (0.1 μg) was reacted with 2.5 μmol iodomercurio-H$_2$DMP (IM-H$_2$DMP) for 30 minutes at 37° C. Following the reaction a change in the ultraviolet absorbance spectra indicative of formation of a new reaction product was observed.

Similar experiments were performed with the thiol containing species glutathione (GSH). In these experiments, 1 μmol GSH was reacted with increasing concentrations of IM-H$_2$DMP (0.02 to 1.0 μmol) and product formation was monitored by absorbance. Again a shift in absorbance spectra was observed indicating the formation of a new reaction product.

The ability to detect a protein on a gel via formation of a fluorescent reaction product comprising a mercurimethyl-dihydropsoralen compound and the protein was also demonstrated. In these experiments, BSA (150 μg) was reacted with the mercurimethyl-dihydropsoralen 3-cyanomercurio-H$_2$DMP (1.5 nmol) for 30 minutes at 37° C. The products were then run on a 10% PAGE gel to separate any reaction product from unreacted psoralen. The fluorescent BSA-mercurimethyl-dihydropsoralen reaction product was mercurimethyl-dihydropsoralen.

Quantification and/or localization of a nucleic acid sequence via a mercurimethyl-dihydropsoralen compound covalently bound to a thiol-containing species was also demonstrated. In these experiments, plasmid double stranded DNA (1 microgram) was run on a 1.2% agarose gel. Afterwards, the gel was soaked in a solution containing the fluorescent reaction product (0.5 μg/ml) of 3-cyano-acetylmercurio-H$_2$DMP and either cysteine or glutathione. After 30 minutes, the gel was soaked in water to remove any reaction product that had not intercalated into the plasmid DNA. The double stranded plasmid DNA was then visualized in the agarose gel on the UV light box and photographed. Alternatively, the plasmid DNA can be preincubated with the fluorescent reaction product and then run on the gel and visualized.

Thus, as demonstrated herein, the mercurimethyl-dihydropsoralen compounds can be used similarly to other dye compounds in accordance with well known techniques to fluorescently label and detect thiol containing species, particularly amino acids, peptides and proteins. In addition, the fluorescently labeled reaction product comprising a thiol containing species and a mercurimethyl-dihydropsoralen compound can be used in accordance with well known techniques to fluorescently label and detect nucleic acids.

Accordingly, one aspect of the present invention relates to a method for detecting any thiol containing species in a sample. In this method, a sample suspected of containing a thiol containing species is contacted with a mercurimethyl-dihydropsoralen compound or derivative thereof at a concentration of mercurimethyl-dihydropsoralen compound or derivative thereof and under conditions which promote binding of the mercurimethyl-dihydropsoralen compound or derivative thereof to any thiol containing species in the sample. In a preferred embodiment, the thiol containing species is incubated with the mercurimethyl-dihydropsoralen or derivative thereof for at least 10 minutes at room temperature. Concentration of the mercurimethyl-dihydropsoralen or derivative thereof to be used for detection of thiol containing species in a sample is dependent upon the experimental conditions and the desired result, but typically ranges from about one nanomolar to one millimolar or more. Optimal concentrations and conditions for detecting thiol containing species in a sample can be determined routinely by those of skill in the art based upon systematic variation until satisfactory staining with minimal background fluorescence is obtained. Formation of a fluorescent signal indicative of thiol containing species in the sample is then monitored, preferably at an excitation wavelength of 415 nm and an emission wavelength of 465 nm for a reaction product of 3-cyano-acetylmercurio-H$_2$DMP and either cysteine or glutathione. The method of the present invention is useful for the sensitive detection of various thiol containing species including, but not limited to, glutathione, cysteine or cystine, and/or methionine content of a sample as well as for detection of total cellular sulfhydryl content.

Another aspect of the present invention relates to new methods for labeling thiol containing species including, but not limited to, amino acids, peptides and proteins. In these methods, the mercurimethyl-dihydropsoralen compound or derivative thereof is contacted with a selected thiol containing species at a concentration and under conditions which promote binding of the mercurimethyl-dihydropsoralen compound or derivative thereof to the thiol containing species. Concentration of the mercurimethyl-dihydropsoralen compound or derivative thereof to be used for labeling is dependent upon the experimental conditions and the desired result, but typically ranges from about one nanomolar to one millimolar or more. Optimal concentrations and conditions for labeling of a selected thiol containing species can be determined routinely by those of skill in the art based upon systematic variation until satisfactory staining with minimal background fluorescence is obtained. Following reaction of the thiol containing species and the mercurimethyl-dihydropsoralen compound or derivative thereof, the fluorescently reaction product is preferably washed to remove residual, excess or unbound mercurimethyl-dihydropsoralen compound or a derivative thereof used for labeling. This aspect of the present invention is particularly useful for fluorescently tagging thiol containing species such as antibodies and enzymes used as detection reagents in other assays.

Thus, another aspect of the present invention relates to fluorescently labeled reaction products comprising a thiol containing species attached to a mercurimethyl-dihydropsoralen compound or a derivative thereof. In a preferred embodiment of this aspect of the present invention, the thiol containing species is an antibody or antibody fragment or an enzyme, which when fluorescently labeled by reaction with the mercurimethyl-dihydropsoralen compound or a derivative thereof, is useful as a detection reagent in other assays.

As demonstrated herein, fluorescently labeled reaction products of the present invention maintain their ability to intercalate nucleic acids. Accordingly, another aspect of the present invention relates to fluorescently labeled reaction products and methods of using these products to detect nucleic acids such as RNA or DNA and to produce fluorescently labeled nucleic acids for use a probes. For these aspects of the present invention, it is preferred that the fluorescently labeled reaction product comprise glutathione or cysteine and a mercurimethyl-dihydropsoralen compound or derivative thereof. For detection of nucleic acids, a sample suspected of containing nucleic acids is contacted with the fluorescently labeled reaction product under conditions which promote intercalation of the mercurimethyl-dihydropsoralen compound or derivative thereof into any nucleic acids in the sample. The sample is then washed and remaining fluorescent products indicative of nucleic acids intercalated with the fluorescently labeled reaction product are detected. Fluorescently labeled nucleic acid probes can be produced in a similar manner by contacting a selected nucleic acid with a fluorescently labeled reaction product comprising the thiol containing species and a mercurimethyl-dihydropsoralen compound or derivative thereof under conditions which promote intercalation of the mercurimethyl-dihydropsoralen compound or derivative thereof into the nucleic acid sequence. Fluorescently labeled nucleic acids are useful as probes in a variety of techniques well known to those skilled in the art.

Another aspect of the present invention relates to kits for fluorescently labeling thiol containing species or nucleic acids and/or detecting thiol containing species or nucleic acids. Kits of the present invention for use in labeling and/or detecting a thiol containing species comprise a mercurimethyl-dihydropsoralen compound or a derivative thereof for fluorescently labeling thiol containing species and/or detecting thiol containing species in a sample. Kits of the present invention for use in labeling and/or detecting nucleic acids comprise a fluorescently labeled reaction product of a thiol containing species covalently attached to a mercurimethyl-dihydropsoralen compound or a derivative thereof. Additional components which can be included in the kits of the present invention include, but are not limited to, reaction buffer such as 10 mM sodium phosphate buffer, pH 6.4 as well as standard solutions of material to be assayed such as glutathione or cysteine.

What is claimed is:

1. A method for detecting a thiol containing species in a sample comprising:
   contacting a sample with a mercurimethyl-dihydropsoralen compound or mercurimethyl-angelicin compound so that a reaction product of the mercurimethyl-dihydropsoralen or the mercurimethyl-angelicin compound and any thiol containing species in the sample is formed; and
   detecting any fluorescence in the sample, wherein fluorescence is indicative of a thiol containing species in the sample.

2. A method for fluorescently labeling a thiol containing species comprising reacting a thiol containing species with a mercurimethyl-dihydropsoralen compound or a mercurimethyl-angelicin compound.

3. A fluorescently labeled reaction product comprising a thiol containing species and a mercurimethyl-dihydropsoralen compound or mercurimethyl-angelicin compound covalently attached thereto.

4. The fluorescently labeled reaction product of claim 3 wherein the thiol containing species is an antibody or an enzyme.

5. A method for detecting nucleic acids in a sample comprising contacting a sample suspected of containing nucleic acid sequences with a fluorescently labeled reaction product comprising a thiol containing species and a mercurimethyl-dihydropsoralen compound or mercurimethyl-angelicin compound so that the fluorescently labeled reaction product intercalates into any nucleic acids in the sample, and detecting fluorescence, wherein fluorescence is indicative of a nucleic acid in the sample.

6. A method for fluorescently labeling a selected nucleic acid comprising contacting a selected nucleic acid with a fluorescently labeled reaction product comprising a thiol containing species and a mercurimethyl-dihydropsoralen compound or a mercurimethyl-angelicin compound so that the fluorescently labeled reaction product intercalates into the selected nucleic acid.

7. A fluorescently labeled nucleic acid comprising a selected nucleic acid intercalated with a fluorescently labeled reaction product comprising a thiol containing species and a mercurimethyl-dihydropsoralen compound or a mercurimethyl-angelicin compound.

8. A kit for fluorescently labeling or detecting thiol containing species comprising a mercurimethyl-dihydropsoralen compound or a mercurimethyl-angelicin compound.

9. A kit for fluorescently labeling or detecting nucleic acids comprising a fluorescently labeled reaction product of mercurimethyl-dihydropsoralen compound or a mercurimethyl-angelicin compound attached to a thiol containing species which intercalates nucleic acids.

* * * * *